United States Patent [19]

Yamagishi et al.

[11] Patent Number: 5,370,865
[45] Date of Patent: Dec. 6, 1994

[54] COMPOSITION FOR USE IN ORAL CAVITY

[75] Inventors: Atsushi Yamagishi, Ichikai; Kazushi Oshino; Ryozo Nakai, both of Utsunomiya; Yasuteru Eguchi, Akatsukashinmachi; Tetsuji Iwasaki; Yuichi Hioki, both of Wakayama, all of Japan

[73] Assignee: KAO Corporation, Tokyo, Japan

[21] Appl. No.: 16,233

[22] Filed: Feb. 11, 1993

[30] Foreign Application Priority Data

May 15, 1992 [JP] Japan ................ 4-123374

[51] Int. Cl.$^5$ ................ A61K 7/16; A61K 7/22
[52] U.S. Cl. ................ 424/54; 424/49; 424/52; 424/57
[58] Field of Search ................ 424/49–57

[56] References Cited

U.S. PATENT DOCUMENTS

| | | | |
|---|---|---|---|
| 3,864,472 | 2/1975 | Pensak et al. | 424/54 |
| 4,036,950 | 7/1977 | Baines et al. | 424/54 |
| 4,064,138 | 12/1977 | Samri et al. | 548/344 |
| 4,152,421 | 5/1979 | Tsutsumi et al. | 424/57 |
| 4,256,731 | 3/1981 | Curtis et al. | 424/54 |
| 4,391,798 | 7/1983 | Tavss et al. | 424/52 |
| 4,536,519 | 8/1985 | Suzuki et al. | 514/785 |
| 4,670,575 | 6/1987 | Kurosaki et al. | 558/146 |
| 4,776,976 | 10/1988 | Nakamura et al. | 252/312 |
| 4,820,507 | 4/1989 | Klueppel et al. | 424/54 |
| 4,868,163 | 9/1989 | Takei et al. | 514/76 |
| 4,997,672 | 3/1991 | DeSimone et al. | 426/649 |
| 5,019,373 | 5/1991 | Carter et al. | 424/52 |
| 5,035,881 | 7/1991 | Mori et al. | 424/54 |
| 5,064,640 | 11/1991 | Kleber et al. | 424/52 |
| 5,085,854 | 2/1992 | Fukuda et al. | 424/63 |
| 5,128,122 | 7/1992 | Cerami et al. | 424/49 |

FOREIGN PATENT DOCUMENTS

| | | |
|---|---|---|
| 0150374 | 8/1985 | European Pat. Off. . |
| 0371542 | 6/1990 | European Pat. Off. . |
| 2192801 | 2/1974 | France . |
| 2600708 | 7/1976 | Germany . |
| 2744980 | 4/1978 | Germany . |
| 180496 | 12/1988 | Japan . |
| 1431932 | 4/1976 | United Kingdom . |

OTHER PUBLICATIONS

Moncrieff "The Chemical Senses" (1944) pp. 388, 102, 107, 237, 238, 247, 266, 271, 273, 275.
Inglett "Symposium Sweetners" (1974) pp. 235, 30, 135, 138.
Bender "Amino Acid Metabolism" (1975) pp. 203–208.
Zapsalis "Food Chemistry and Nutritional Biomchemistry" (1985) pp. 581–591.

Primary Examiner—Shep K. Rose
Attorney, Agent, or Firm—Oblon, Spivak, McClelland, Maier, & Neustadt

[57] ABSTRACT

A composition for use in the oral cavity comprising a monophosphate represented by the following general formula (1), $$R^1-(OCH_2CH_2)_n-O-\overset{O}{\underset{OX^2}{\overset{\|}{P}}}-OX^1 \quad (1)$$

wherein $R^1$ is a linear or branched alkyl or alkenyl group with 6 to 20 carbon atoms, and may have a substituted fluorine atom; one of $X^1$ or $X^2$ is a basic amino acid residual group, while the other is a hydrogen atom, an alkali metal, an ammonium, an alkyl amine, an alkanol amine, or a basic amino acid residual group; and n is an integer from 0 to 4. The composition exhibits a superior action in protecting the tooth surface, is stable, and has a pleasant taste.

10 Claims, No Drawings

COMPOSITION FOR USE IN ORAL CAVITY

BACKGROUND OF THE INVENTION

1. Field of the Invention

The present invention relates to a composition for use in the oral cavity, which comprises a phosphoric ester, exhibits a superior action in protecting the tooth surface, is stable, and has a pleasant taste.

2. Description of Background Art

Phosphoric esters (hereinafter referred to as "AP") cause very little irritation, and exhibit a superior effect in restraining the build up of plaque on the tooth and in preventing dental caries by forming a film on the surface of the tooth for improving the tooth's resistance to acidity. Accordingly, the utilization of AP in a composition for use in the oral cavity has been conventionally proposed. For example, a toothpaste containing a salt of monoalkyl phosphate as a foaming agent, which does not change taste or flavor of foods and beverages is disclosed in Japanese Patent Laid-open (kokai) 47542/1978 (U.S. Pat. No. 4,152,421). Japanese Patent Application (kokoku) No. 500061/1979 (U.S. Pat. No. 4,366,146) discloses a toothpaste composition for preventing the formation of spots, which contains a monoalkyl phosphate as a film-forming material. Japanese Patent Laid-open (kokai) No. 200619/1990 (U.S. Pat. No. 5,019,373) discloses an aqueous composition suitable for use as a dentifrice and as a gargle, comprising a medium-chain dialkyl phosphate, a long-chain dialkyl phosphate, and a monoalkyl phosphate. This composition provides superior decay-resistant activity and does not change flavor or taste of foods and beverages. U.S. Pat. No. 4,036,950 discloses a dentifrice containing an abrasive, a cationic germicide, and polyoxyethylenealkylether phosphate.

When actually manufacturing a composition for use in the oral cavity into which AP is blended, a basic compound is used to neutralize the phosphoric acid group. Conventionally, an alkali metal, an alkaline earth metal, or an alkyl amine is used for this purpose. The use of these basic compounds, however, entails the following problems.

Specifically, an alkali metal salt of AP has a high Krafft point, crystallizes in the formulation, and becomes non-uniform, impairing the stability of the product. Accordingly, it is difficult to apply an alkali metal salt to a transparent, uniform type of mouthwash. In addition, an alkyl amine salt of AP and an alkanol amine salt of AP are strongly irritant, even though they have a low Krafft point. Thus, their safety is a problem. Furthermore, the taste of AP is generally unpleasant, leaving a bitter aftertaste.

A basic amino acid salt of AP is a conventionally known compound. For example, in Japanese Patent Laid-open (kokai) No. 180496/1983, an arginine salt of a phosphate and an emulsifier containing this salt are disclosed. In Japanese Patent Laid-open (kokai) No. 319410/1989 (U.S. Pat. No. 5,085,854) a semitransparent emulsified cosmetic composition containing an arginine salt of monoalkyl phosphate, a nonionic surfactant, an oil component, and water is disclosed. However, all of these prior arts merely propose incorporation of an arginine salt of monoalkyl phosphate into cosmetics as an emulsifier. No prior arts disclose the possibility of blending a basic amino acid salt of AP into a composition for use in the mouth cavity.

An object of the present invention is to provide a composition containing AP for use in the oral cavity which exhibits a superior action in protecting the tooth surface, is stable, and has a pleasant taste.

The inventors of the present invention have undertaken painstaking investigations and found that by using a basic amino acid such as arginine or lysine or the like to neutralize an AP it is possible to obtain a composition for use in the oral cavity, of which the Krafft point of the composition is lowered, which is stable without being colored even when stored for a long period of time, and is suitable for use in protecting the tooth surface, and also has an improved taste.

SUMMARY OF THE INVENTION

Specifically, the above object is achieved in the present invention by the provision of a composition for use in the oral cavity comprising a monophosphate represented by the following general formula (1),

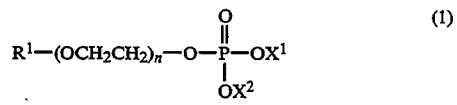

wherein $R^1$ is a linear or branched alkyl or alkenyl group with 6 to 20 carbon atoms, and may have a substituted fluorine atom; one of $X^1$ or $X^2$ is a basic amino acid residual group, while the other is a hydrogen atom, an alkali metal, an ammonium, an alkyl amine, an alkanol amine, or a basic amino acid residual group; and n is an integer from 0 to 4.

The above object is further achieved in the present invention by the provision of a composition for use in the oral cavity comprising:

(A) a monophosphate represented by the following general formula (2),

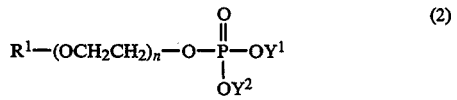

wherein $R^1$ is a linear or branched alkyl or alkenyl group with 6 to 20 carbon atoms, and may have a substituted fluorine atom; $y^1$ or $y^2$ may be the same or different and represent a hydrogen atom, an alkali metal, an ammonium, an alkyl amine, or an alkanol amine; and n is an integer from 0 to 4, and (B) a basic amino acid.

Other objects, features and advantages of the invention will hereinafter become more readily apparent from the following description.

DETAILED DESCRIPTION OF THE INVENTION AND PREFERRED EMBODIMENTS

Examples of the linear or branched alkyl or alkenyl groups with 6 to 20 carbon atoms which may have a substituted fluorine atom and is represented by $R^1$ in the monophosphates of the general formulas (1) and (2) used in the present invention include hexyl group, octyl group, decyl group, dodecyl group, tetradecyl group, hexadecyl group, octadecyl group, eicosyl group, 2-ethylhexyl group, dodecenyl group, oleyl group, elaidyl group, and the like. Among these, as $R^1$, an alkyl group with 8 to 20 carbon atoms is preferable, 10 to 20 carbon atoms especially preferable, 12 to 16 carbon atoms more preferable, and 14 carbon atoms most preferable. Either one kind of alkyl or alkenyl group with a single chain length or a mixture of a plurality of alkyl or alkenyl groups with different chain lengths may be used.

The basic amino acids which can be used include not only naturally occurring basic amino acids, such as arginine, lysine, and histidine, but also any basic amino acids having a carboxyl group and an amino group in the molecule, which are water-soluble and provide an aqueous solution with a pH of 7 or greater. Among these, arginine is particularly desirable.

The monophosphate (1) used in the present invention can be manufactured by any commonly-known method. An example of such a manufacturing method is a method comprising submitting a commercially available monophosphate (2) to alkaline conditions, desalting it by electrodialysis, and neutralizing the product with the basic amino acid (B). An alkali metal salt, an amine salt, or an organic amine salt may be included during the neutralization to the extent that the neutralization is not hindered. The molar ratio of the basic amino acid (B) to the monophosphate (2) is preferably (B)/(2)=0.8 to 2.0, more preferably 1.0 to 1.8, and most preferably 1.1 to 1.4.

In the present invention, the composition for use in the oral cavity may be prepared by formulating the monophosphate (1) obtained using the above method. However, it is also possible to form a composition comprising the above-mentioned components (A) and (B) and then to effect the neutralization in the composition. When both the component (A) and the component (B) are contained in the blend, the ratio by mol of the component (B) to the component (A) is preferably (B)/(A)=0.8 to 2.0, more preferably 1.0 to 1.8, and most preferably 1.1 to 1.4. In the latter case, it is presumed that the component (A) and the component (B) react together within the resulting composition to produce the monophosphate (1).

The amount of the monophosphate (1) or (2) in the composition for use in the oral cavity of the present invention is 0.001 to 50% by weight (hereinafter % refers to % by weight), preferably 0.05 to 10%, even more preferably 0.1 to 5%, and most preferably 0.1 to 3%. If the amount is less than 0.001%, protecting the tooth surface is weakened; if greater than 50%, the stability of the formulation is poor.

Beside the above-mentioned essential components, the composition of the present invention may contain commonly used vehicles for the oral cavity to the extent that the effect of the invention is not adversely affected. The composition can be formulated into toothpaste, toothpowder, liquid dentifrice, mouthwash, gargle, mouth rinse, gum massage cream, troches, chewing gum, candies, or the like.

Among these, liquid compositions such as mouthwash, mouth rinse, and gargle, or compositions in solid or paste form such as toothpaste, toothpowder, liquid dentifrice, gum massage cream, troches, and the like are preferable.

Examples of the aforementioned vehicles for the oral cavity which can be used in the composition of the present invention include abrasives, thickening agents, moisturizers, surfactants, perfumes, sweeteners, preservatives, colorants, water, germicides, water-soluble fluorine-containing compounds, silicone, and other effective ingredients.

Examples of abrasives include hydrogen calcium phosphate, calcium pyrophosphate, calcium carbonate, insoluble sodium metaphosphate, potassium metaphosphate, silicic acid anhydride, silicic acid hydrate, aluminum silicate, zirconium silicate, bentonite, zeolite, aluminum oxide, aluminum hydroxide, resins and mixtures of these. Among these, silicic acid anhydride, silicic acid hydrate, calcium carbonate, zeolite and aluminum oxide are preferable.

Examples of thickening agents include sodium carboxymethyl cellulose, methyl cellulose, hydroxyethyl cellulose, arginates, carrageenan, gum arabic, polyvinyl alcohol, gum tragacanth, starch, sodium polyacrylate, and the like.

Examples of moisturizers include polyethylene glycol, propylene glycol, sorbitol, glycerine, maltitol, xylitol, and the like. Of these, glycerine and sorbitol are preferable.

The surfactant is used as a foaming agent or a stabilizing agent for an oil-containing material. Various types of surfactants other than phosphates may be used. Examples of preferable surfactants include sodium alkyl sulfate, sodium alkylbenzenesulfonate, sodium N-acylsarcosinate, N-acylglutamates, polyoxyethylene hydrogenated castor oil, polyoxyethylene-polyoxypropylene block copolymers (Pluronic type), fatty acid esters of sucrose, alkylglycosides, fatty acid esters of sorbitan, fatty acid esters of polyoxyethylenesorbitan, alkyldimethylamine oxide, carbobetaine, hydroxycarbobetaine, phosphobetaine, hydroxyphosphobetaine, sulfobetaine, hydroxysulfobetaine, and the like. Of these, water-soluble nonionic and amphoteric surfactants such as polyoxyethylene hydrogenated castor oil, polyoxyethylene-polyoxypropylene block copolymers, fatty acid esters of sucrose, alkylglycosides, fatty acid esters of sorbitan, and fatty acid esters of polyoxyethylenesorbitan, are particular preferable.

Examples of perfumes include natural perfumes such as spearmint oil, peppermint oil, wintergreen oil, sassafras oil, clove oil, sage oil, eucalyptus oil, mayonara oil, cinnamon oil, thyme oil, lemon oil, orange oil, and the like; as well as synthetic perfumes such as 1-menthol, anethole, carvone, eugenol, thymol, methyl salicylate, and the like. Examples of sweeteners include saccharin, saccharin sodium, stevioside, neohesperidyldihydrocarcone, beruraruchine, p-methoxycinnamic aldehyde, glycyrrhizinates, aspartame (methyl aspartylphenylalanine), and the like. Typical germicides which can be used are chlorhexidines, quaternary ammonium salts, triclosan, alkyldiaminoethylglycine hydrochloride, and the like. Examples of preservatives include benzoic acid, sodium benzoate, parahydroxybenzoic esters, and the like. Water-soluble fluorine-containing compounds which can be used include sodium fluoride, sodium monofluorophosphate, and the like. Other effective ingredients include chlorophyll compounds, sodium chloride, vitamin C, vitamin E, nicotinic acid esters, allantoinchlorohydroxy aluminum, azulene, lysozyme chloride, hinokitiol, $\beta$-glycyrrhetinic acid, dipotassium glycyrrhizinate, protease, materials extracted from herbal medicines, and the like.

The amounts of these oral vehicles blended into the composition of the present invention vary according to the formulation. In the case of a liquid composition, any vehicles among the above-mentioned oral vehicles can be incorporated with the exception of the abrasive and the thickening agent. In principle, it is desirable to incorporate 0.05 to 10% of the monophosphate (1) or (2), 1 to 30% of the moisturizer, and 50 to 96% of alcohol and water. The ratio of alcohol and water is preferably 1:1 to 200:1, and more preferably 5:1 to 100:1. The amount of alcohol in the composition is preferably 1 to 20%.

When the composition is in the form of a paste, all of the above-mentioned vehicles can be incorporated. In principle, it is preferable to incorporate 0.05 to 10% of the monophosphate (1) or (2), 10 to 75% of the abrasive, 0.5 to 5% of the thickening agent, and 10 to 85% of the moisturizer and water. The abrasive is preferably 20 to 75% in the case of a toothpaste, and 10 to 30% in the case of a liquid dentifrice.

For a solid composition such as a toothpowder, the solid ingredients among the above-mentioned vehicles for use in oral cavity can be blended. Basically, it is preferable to use 0.05 to 10% of the monophosphate (1) or (2) and 60 to 99% of the abrasive.

It is preferable that the total content of the perfume and the sweetener in the oral vehicle be 0.01 to 5%. The pH of the composition of the present invention is in the range of 5 to 9.5, preferably, in the range of 6 to 8.

A solid composition such as a toothpowder used as the composition of the present invention can normally be formulated by mechanically blending the above-mentioned solid ingredients. A composition in the form of a paste can normally be formulated by mechanically blending the various ingredients with deaeration.

In order to protect the surface of the teeth, utilizing the composition for use in the oral cavity of the present invention, the composition is, in principle, preferably applied about 1-3 times per day, about five days a week. Among the forms of the composition, a mouth rinse is the most desirable. Good protection can be provided to the tooth surface by using about 10 ml of the mouth rinse of the present invention after brushing, holding in the mouth for about 30 seconds, then ejecting.

The composition for use in the oral cavity of the present invention provides superior protection to the tooth surface, is stable, and, furthermore, has a pleasant taste.

Other features of the invention will become apparent in the course of the following description of the exemplary embodiments which are given for illustration of the invention and are not intended to be limiting thereof.

EXAMPLES

Examples 1-2, Comparative Examples 1-2

Compositions for mouthwash were prepared according to the formulation given in Table 1 and stored under the conditions shown in Table 2 to test their stability. The results are given in Table 2. The flavor and taste was evaluated by the method described below. The results are shown in Table 3.

<Method for evaluation of flavor and taste>

Evaluation was performed by a panel of 20 persons. Ten ml of the mouthwash were held in the mouth for 30 seconds and the impression at that time was evaluated as one of three grades, O, D, or X. A composition receiving 70% or more response that the taste was good was graded O; above 40% but less than 70% was graded D; less than 40% was graded X. Since the composition of Comparative Example 1 deposited crystals at temperatures below 30° C., its evaluation was carried out after adjusting the sample temperature at 35° C.

TABLE 1

|  | Example 1 | Example 2 | Comparative Example 1 | Comparative Example 2 |
|---|---|---|---|---|
| Sorbitol | 15.0 | 15.0 | 15.0 | 15.0 |
| Ethanol | 5.0 | 5.0 | 5.0 | 5.0 |
| AP ($C_{12}$)* | 0.5 | 0.5 | 0.5 | 0.5 |
| Polyoxyethylene (EO = 60) hydrogenated castor oil | 0.2 | 0.2 | 0.2 | 0.2 |
| Methyl p-hydroxybenzoate | 0.05 | 0.05 | 0.05 | 0.05 |
| L-Arginine | 0.4 | — | — | — |
| L-Lysine | — | 0.34 | — | — |
| 10% NaOH aqueous solution | — | — | 0.84 | — |
| Triethanolamine | — | — | — | 0.34 |
| Perfume | 0.15 | 0.15 | 0.15 | 0.15 |
| Purified water | Balance | Balance | Balance | Balance |
| Total | 100 | 100 | 100 | 100 |

*Monoalkyl phosphate ($C_{12}$)

TABLE 2

|  | Immediately after blending Room temperature (20° C.) | Immediately after blending −5° C. | After storing at 40° C. 6 months |
|---|---|---|---|
| Example 1 | O | O | O |
| Example 2 | O | O | O |
| Comparative Example 1 | X (Crystals deposited) | X | X |
| Comparative Example 2 | O | O | X (Colored brown) |

Evaluation
O: No change
X: Changed

TABLE 3

|  | Taste during mouthwash | Taste after mouthwash |
|---|---|---|
| Example 1 | O | O |
| Example 2 | O | O |
| Comparative Example 1 | D | X |
| Comparative Example 2 | X | X |

Compositions for use in mouth cavity of Examples 3-10 were prepared according to formulations given in respective Examples.

| Example 3 (Mouthwash) | |
|---|---|
| Sorbit solution | 15.0% |
| Ethanol | 5.0 |
| Monoalkyl phosphate ($C_{12}$) | 0.5 |
| Polyoxyethylene (EO = 60) hydrogenated castor oil | 0.2 |
| Methyl p-hydroxybenzoate | 0.05 |
| L-Arginine | 0.4 |
| Chlorhexidine hydrochloride | 0.01 |
| Perfume | 0.2 |
| Purified water | Balance |
| Total | 100% |
| Example 4 (Mouthwash) | |
| Sorbit solution | 15.0% |
| Ethanol | 7.0 |
| Arginine salt of monoalkyl phosphate ($C_{12}$)* | 0.5 |
| Polyoxyethylene (EO = 40) hydrogenated castor oil | 0.2 |
| Methyl p-hydroxybenzoate | 0.05 |
| Cetylpyridinium chloride | 0.05 |

| | |
|---|---|
| Perfume | 0.15 |
| l-Menthol | 0.05 |
| Purified water | Balance |
| Total | 100% |

*Monoalkyl phosphate/Arginine = 1.1 (equivalent)

Example 5 (Mouthwash)

| | |
|---|---|
| Sorbit solution | 5.0% |
| Ethanol | 5.0 |
| Monoalkyl phosphate ($C_8$) | 0.5 |
| Polyoxyethylene (EO = 25) hydrogenated castor oil | 0.2 |
| Methyl p-hydroxybenzoate | 0.05 |
| L-Lysine | 0.34 |
| Chlorhexidine hydrochloride | 0.01 |
| Sodium fluoride | 0.2 |
| Perfume | 0.2 |
| Purified water | Balance |
| Total | 100% |

Example 6 (Gel-type mouthwash)

| | |
|---|---|
| Sorbit solution | 10.0% |
| Monoalkyl phosphate ($C_{16}$) | 0.5 |
| Polyoxyethylene (EO = 60) hydrogenated castor oil | 0.2 |
| Methyl p-hydroxybenzoate | 0.05 |
| L-Arginine | 0.3 |
| Cetylpyridinium chloride | 0.05 |
| Vitamin E | 0.1 |
| Perfume | 0.15 |
| Purified water | Balance |
| Total | 100.0% % |

Example 7 (Toothpaste)

| | |
|---|---|
| Aluminum hydroxide | 30.0% |
| Sorbit solution | 35.0 |
| Propylene glycol | 5.0 |
| PEG 600 | 2.0 |
| Sodium benzoate | 0.2 |
| Saccharin sodium | 0.1 |
| Sodium monofluorophosphate | 0.7 |
| Silicic acid anhydride | 5.0 |
| Monoalkyl phosphate ($C_{12}$) | 1.5 |
| Hydroxyethyl cellulose | 0.8 |
| L-Arginine | 1.2 |
| Glycyrrhetinic acid | 0.1 |
| Perfume | 0.9 |
| Purified water | Balance |
| Total | 100.0% % |

Example 8

| | |
|---|---|
| Aluminum hydroxide | 45.0% |
| Sorbit solution | 25.0 |
| Propylene glycol | 5.0 |
| PEG 600 | 2.0 |
| Sodium benzoate | 0.2 |
| Saccharin sodium | 0.1 |
| Sodium monofluorophosphate | 0.7 |
| Silicic acid anhydride | 3.0 |
| Monoalkyl phosphate ($C_{12}$) | 1.5 |
| Hydroxyethyl cellulose | 0.8 |
| L-Lysine | 1.0 |
| Triclosan | 0.3 |
| Perfume | 0.9 |
| Purified water | Balance |
| Total | 100.0% % |

Example 9 (Toothpaste)

| | |
|---|---|
| Alumina | 30.0% |
| Sorbit solution | 35.0 |
| Propylene glycol | 5.0 |
| PEG 600 | 2.0 |
| Sodium benzoate | 0.2 |
| Saccharin sodium | 0.1 |
| Sodium monofluorophosphate | 0.7 |
| Silicic acid anhydride | 7.5 |
| Monoalkyl phosphate ($C_{14}$) | 1.5 |
| L-Arginine | 1.1 |
| Hydroxyethyl cellulose | 1.5 |
| Zinc oxide | 0.1 |
| Perfume | 0.9 |
| Purified water | Balance |
| Total | 100.0% % |

Example 10 (Toothpaste)

| | |
|---|---|
| Silicic acid hydrate | 30.0% |
| Sorbit solution | 30.0 |
| Glycerine | 5.0 |
| PEG 600 | 3.0 |
| Sodium benzoate | 0.2 |
| Saccharin sodium | 0.1 |
| Sodium fluoride | 0.2 |
| Silicic acid anhydride | 15.0 |
| Arginine salt monoalkyl phosphate ($C_{12}$)* | 1.5 |
| Carboxymethyl cellulose | 1.0 |
| Zinc oxide | 0.1 |
| Perfume | 0.9 |
| Purified water | Balance |
| Total | 100.0% % |

*Monoalkyl phosphate/Arginine = 1.3 (equivalent)

Example 11 (Mouthwash)

The following oil components and water components were dissolved separately and two solutions were mixed to obtain a transparent mouthwash composition. Preferable use of this composition is holding it in mouth after blushing teeth for about 30 seconds and then ejecting.

| | |
|---|---|
| (Oil components) | |
| Monoalkyl phosphate ($C_{14}$) | 0.25% |
| Polyoxyethylene (EO = 20) sorbitan monostearate | 0.10 |
| Methyl p-hydroxybenzoate | 0.05 |
| Ethanol | 4.00 |
| Perfume | 0.12 |
| (Water component) | |
| L-Arginine | 0.23 |
| Sorbit solution (70%) | 8.00 |
| Glycerine | 8.00 |
| Saccharin sodium | 0.01 |
| Benzalkonium chloride | 0.05 |
| Purified water | Balance |
| Total | 100.0% % |

Obviously, numerous modifications and variations of the present invention are possible in light of the above teachings. It is therefore to be understood that within the scope of the appended claims, the invention may be practiced otherwise than as specifically described herein.

What is claimed is:

1. A composition for use in the oral cavity comprising a monophosphate represented by the following general formula (1),

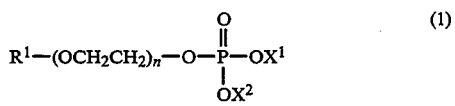

wherein $R^1$ is a linear or branched alkyl or alkenyl group with 6 to 20 carbon atoms, and may have a substituted fluorine atom; one of $X^1$ or $X^2$ is a basic amino acid group, while the other is a hydrogen atom, an alkali metal, an ammonium, an alkyl amine, an alkanol amine, or a basic amino acid group; and n is an integer from 0 to 4, wherein said basic amino acid is selected from the group consisting of arginine, lysine, and histidine, said composition being storage stable and pleasant tasting.

2. A composition for use in the oral cavity comprising:

(a) a monophosphate represented by the following formula (1),

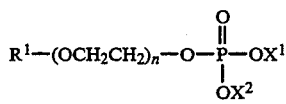

wherein $R^1$ is a linear or branched alkyl or alkenyl group with 6 to 20 carbon atoms, and may have a substituted fluorine atom; one of $X^1$ or $X^2$ is a basic amino acid group, while the other is a hydrogen atom, an alkali metal, an ammonium, an alkyl amine, an alkanol amine, or a basic amino acid group; and n is an integer from 0 to 4, and (b) a vehicle for use in oral cavity, wherein said basic amino acid is selected from the group consisting of arginine, lysine, and histidine, said composition being storage stable and pleasant tasting.

3. A liquid composition for use in the oral cavity comprising:

(a) a monophosphate represented by the following formula (1),

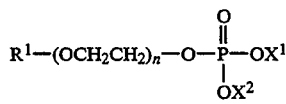

wherein $R^1$ is a linear or branched alkyl or alkenyl group with 6 to 20 carbon atoms, and may have a substituted fluorine atom; one of $X^1$ or $X^2$ is a basic amino acid group, while the other is a hydrogen atom, an alkali metal, an ammonium, an alkyl amine, an alkanol amine, or a basic amino acid group; and n is an integer from 0 to 4, (b) a moisturizing agent,
    (c) an alcohol, and
    (d) water, wherein said basic amino acid is selected from the group consisting of arginine, lysine, and histidine, said composition being storage stable and pleasant tasting.

4. A paste composition for use in the oral cavity comprising:

(a) a monophosphate represented by the following formula (1),

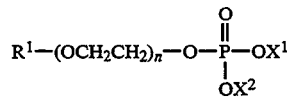

wherein $R^1$ is a linear or branched alkyl or alkenyl group with 6 to 20 carbon atoms, and may have a substituted fluorine atom; one of $X^1$ or $X^2$ is a basic amino acid group, while the other is a hydrogen atom, an alkali metal, an ammonium, an alkyl amine, an alkanol amine, or a basic amino acid group; and n is an integer from 0 to 4

(b) an abrasive,
    (c) a thickening agent,
    (d) a moisturizing agent, and
    (e) water, wherein said basic amino acid is selected from the group consisting of arginine, lysine, and histidine, said composition being storage stable and pleasant tasting.

5. A composition for use in the oral cavity comprising:

(A) a monophosphate represented by the following general formula (2),

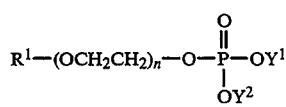

wherein $R^1$ is a linear or branched alkyl or alkenyl group with 6 to 20 carbon atoms, and may have a substituted fluorine atom; $y^1$ or $y^2$ may be the same or different and represent a hydrogen atom, an alkali metal, an ammonium, an alkyl amine, or an alkanol amine; and n is an integer from 0 to 4, and (B) a basic amino acid, wherein said basic amino acid is selected from the group consisting of arginine, lysine, and histidine, said composition being storage stable and pleasant tasting.

6. A composition for use in the oral cavity comprising:

(A) a monophosphate represented by the following general formula (2),

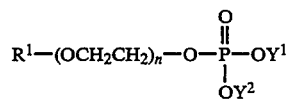

wherein $R^1$ is a linear or branched alkyl or alkenyl group with 6 to 20 carbon atoms, and may have a substituted fluorine atom; $y^1$ or $y^2$ may be the same or different and represent a hydrogen atom, an alkali metal, an ammonium, an alkyl amine, or an alkanol amine; and n is an integer from 0 to 4, (B) a basic amino acid, and
    (C) a vehicle for use in oral cavity, wherein said basic amino acid is selected from the group consisting of arginine, lysine, and histidine, said composition being storage stable and pleasant tasting.

7. A liquid composition for use in the oral cavity comprising:

(A) a monophosphate represented by the following general formula (2),

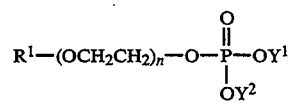

wherein $R^1$ is a linear or branched alkyl or alkenyl group with 6 to 20 carbon atoms, and may have a substituted fluorine atom; $y^1$ or $y^2$ may be the same or different and represent a hydrogen atom, an alkali metal, an ammonium, an alkyl amine, or an alkanol amine; and n is an integer from 0 to 4, (B) a basic amino acid,
    (C) a moisturizing agent,
    (D) an alcohol, and
    (E) water, wherein said basic amino acid is selected from the group consisting of arginine, lysine, and histidine, said composition being storage stable and pleasant tasting.

8. A paste composition for use in the oral cavity comprising:

(A) a monophosphate represented by the following general formula (2),

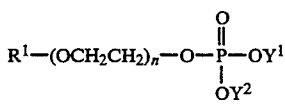 (2)

wherein $R^1$ is a linear or branched alkyl or alkenyl group with 6 to 20 carbon atoms, and may have a substituted fluorine atom; $y^1$ or $y^2$ may be the same or different and represent a hydrogen atom, an alkali metal, an ammonium, an alkyl amine, or an alkanol amine; and n is an integer from 0 to 4, (B) a basic amino acid,
(C) an abrasive,
(D) a thickening agent,
(E) a moisturizing agent, and
(F) water, wherein said basic amino acid is selected from the group consisting of arginine, lysine, and histidine, said composition being storage stable and pleasant tasting.

9. A method of protecting teeth comprising applying to the oral cavity a monophosphate represented by the following general formula (1),

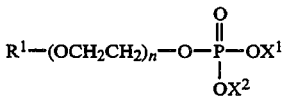 (1)

wherein $R^1$ is a linear or branched alkyl or alkenyl group with 6 to 20 carbon atoms, and may have a substituted fluorine atom; one of $X^1$ or $X^2$ is a basic amino acid group, while the other is a hydrogen atom, an alkali metal, an ammonium, an alkyl amine, an alkanol amine, or a basic amino acid group; and n is an integer from 0 to 4, wherein said basic amino acid is selected from the group consisting of arginine, lysine, and histidine, said composition being storage stable and pleasant tasting.

10. A method of protecting teeth comprising applying to the oral cavity a composition for use in the oral cavity comprising:

(A) a monophosphate represented by the following formula (2),

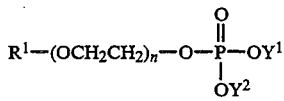 (2)

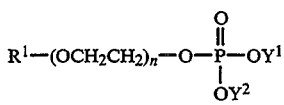 (2)

wherein $R^1$ is a linear or branched alkyl or alkenyl group with 6 to 20 carbon atoms, and may have a substituted fluorine atom; $y^1$ or $y^2$ may be the same or different and represent a hydrogen atom, an alkali metal, an ammonium, an alkyl amine, or an alkanol amine; and n is an integer from 0 to 4, and (B) a basic amino acid, wherein said basic amino acid is selected from the group consisting of arginine, lysine, and histidine, said composition being storage stable and pleasant tasting.

* * * * *